United States Patent [19]

Graves

[11] Patent Number: 4,635,660
[45] Date of Patent: Jan. 13, 1987

[54] ANIMATED DENTAL FLOSS DISPENSER

[75] Inventor: Rodney J. Graves, Phoenix, Ariz.

[73] Assignee: E & J Enterprises, Inc., Phoenix, Ariz.

[21] Appl. No.: 794,680

[22] Filed: Nov. 4, 1985

[51] Int. Cl.⁴ .............................................. A61C 15/00
[52] U.S. Cl. .................................... 132/92 A; 132/91; 40/421
[58] Field of Search .............. 132/92 A, 91, 89, 92 R, 132/90; 40/421

[56] References Cited

U.S. PATENT DOCUMENTS

| 1,650,630 | 11/1927 | Klein | 40/421 |
| 2,053,351 | 9/1936 | Stenger | 40/421 |
| 2,295,430 | 9/1942 | Seewald | 40/421 |
| 2,926,487 | 3/1960 | Stone | 40/421 |
| 3,225,472 | 12/1965 | Guida | 40/421 |
| 3,746,017 | 7/1973 | Casselman | 132/92 A |
| 4,308,880 | 1/1982 | Graves | 132/92 A |

Primary Examiner—John J. Wilson
Attorney, Agent, or Firm—Warren F. B. Lindsley

[57] ABSTRACT

An animated dental floss dispenser which simulates the flossing of a person's teeth as the dental floss is withdrawn, the animation being produced by a particularly simple and inexpensive mechanism.

8 Claims, 12 Drawing Figures

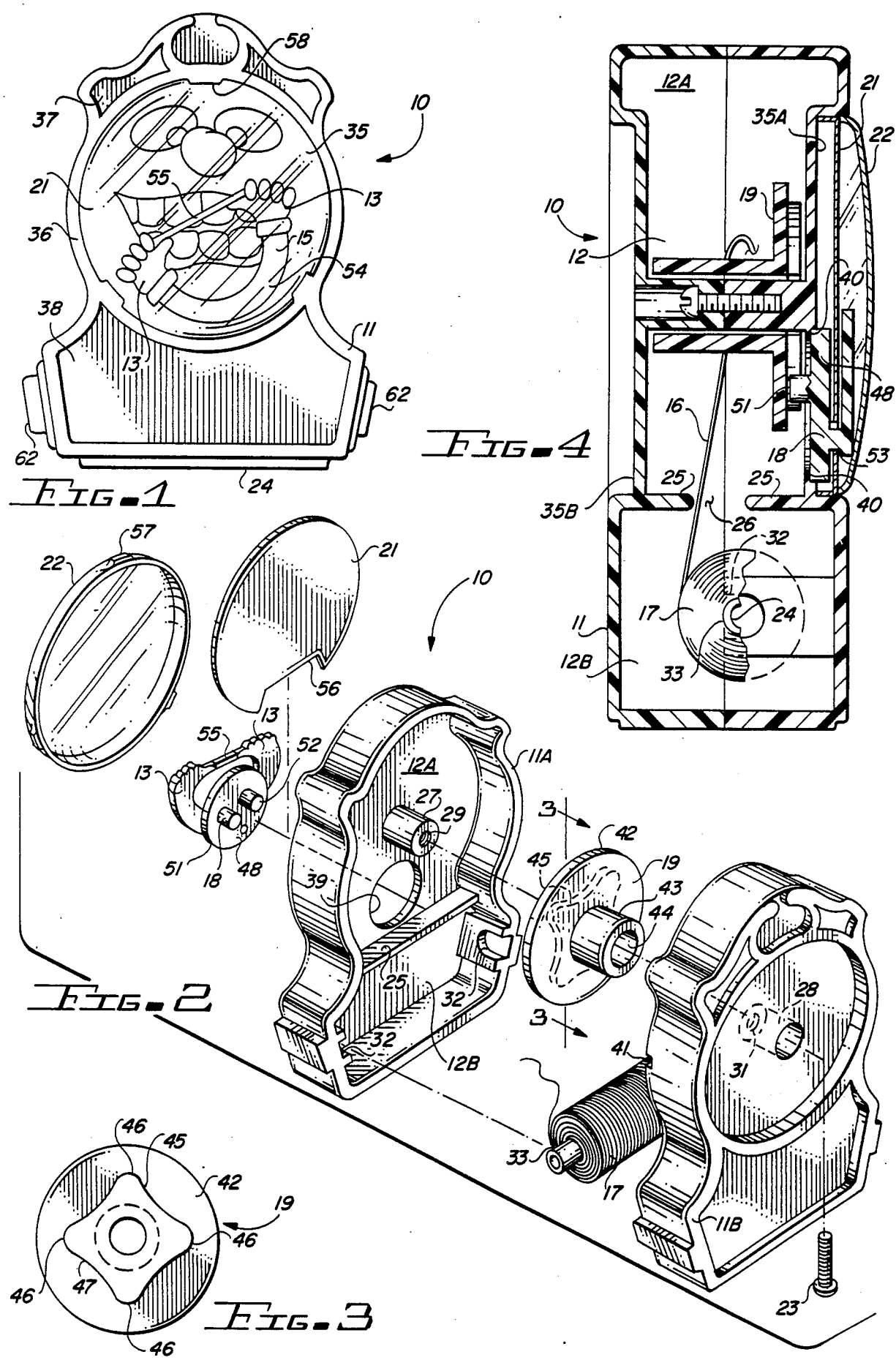

ANIMATED DENTAL FLOSS DISPENSER

BACKGROUND OF THE INVENTION

It is an established fact that the periodic use of dental floss for disorganizing bacterial plaque always present in tiny crevices near the gum line and between the teeth is recommended by dental authorities as a necessary oral hygiene practice.

Many attempts have been made to make a convenient dispenser for dental floss but most have been merely storage and dispensing devices for floss and few, if any, have been animated in such a way as to encourage the flossing process, especially for children and young adults.

FIELD OF THE INVENTION

In view of the importance of performing the flossing function at specified periodic intervals of time, and because the average person is inclined to be apathetic or forgetful about the importance of the precise timing of such functions, a need exists for a suitable reminder means which will also stimulate the viewer to action. It is also evident that if the necessary material, such as dental floss, is conveniently at hand when needed, it would greatly assist in the performance of the flossing function at the proper time.

DESCRIPTION OF THE PRIOR ART

Various types of timing and dispensing devices have been used for this purpose, such as clocks that may be set to emit a sound at the proper time to get the user's attention and separate dispensing means for the material required.

In such usage, considerable difficulty is usually encountered in coordinating the function of the separated timing and dispensing devices because they are often kept in different rooms of the user's home and the sound emitted by the time clock may not be audible to the user at all times.

Therefore, a need exists for a dispensing device that calls the user's attention to the fact that the time has arrived for the performance of oral hygiene implemented by the material dispensed by the device.

U.S. Pat. No. 3,746,017 is directed to a dental floss holder and applicator having a floss storage and dispensing reel, floss take-up reel and an arcuate arm to hold floss in application position. This device does not, however, incorporate any means for encouraging the use of the dispenser or the flossing of the teeth.

U.S. Pat. No. 4,308,880, issued to the author of the present invention, does incorporate an animated figure that moves in simulation of the flossing action as a means for encouraging the use of the dispenser, but this device is relatively complex in its structure and in terms of the number of individual parts involved. For this reason, the manufacturing cost is excessive.

What is needed is a device that is similar in function to the dispenser of U.S. Pat. No. 4,308,880, but simpler in structure and less expensive.

SUMMARY OF THE INVENTION

In accordance with the invention claimed, a new and improved animated dental floss dispenser is provided which is capable of visually simulating the flossing of a person's teeth and the simultaneous dispensing of dental floss.

It is, therefore, one object of this invention to provide a new and improved dental floss dispenser.

Another object of this invention is to provide a new and improved animated dental floss dispenser which visually simulates the flossing of a person's teeth while simultaneously dispensing dental floss.

A further object of this invention is to provide a dental floss dispenser which by its appearance stimulates a viewer to floss his or her teeth.

A still further object of this invention is to provide a new and improved dental floss dispenser which utilizes a simulated version of a person's teeth and mouth together with movable hands simulating a flossing action to encourage young and old to floss their teeth.

A still further object of this invention is to provide an easily portable dispenser that can be hand carried wherever needed.

Yet another object of this invention is to provide such a dispenser in a form that utilizes but a small number of inexpensive parts in a relatively simple mechanism that is inexpensive to manufacture.

Further objects and advantages of the invention will become apparent as the description is given and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 1 is a frontal view of an animated dental floss dispenser, embodying the invention, the dispenser simulating the flossing of a person's teeth as the dental floss is withdrawn;

FIG. 2 is an exploded view of the dental floss dispenser of FIG. 1;

FIG. 3 is a plan view of a cam wheel incorporated in the dispenser of FIG. 1 as an element of the mechanism which actuates the animated flossing action of the dispenser;

FIG. 4 is a cross-sectional side view of the dispenser of FIGS. 1 and 2;

DESCRIPTION OF THE PREFERRED EMBODIMENT

Figure 5:
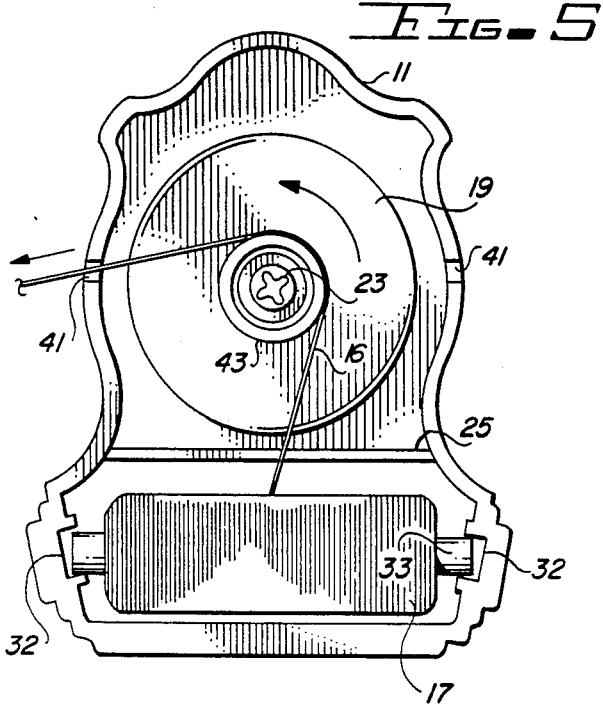
FIG. 5 is a cross-sectional rear view of the dispenser of FIGS. 1-4.

Referring more particularly to the drawings by characters of reference, FIGS. 1-12 disclose an animated dental floss dispenser 10 having a housing 11 defining a cavity 12 in which the floss and the mechanism for moving the hands 13 of the animated character 14 are mounted.

The purpose of the dispenser is to encourage the removal of dental floss from the dispenser, thereby also encouraging the use of the floss in cleaning the teeth and gums. To encourage the removal of dental floss from the dispenser, the animated character is provided with arms and hands, the hands apparently holding a strip of floss in position for flossing the teeth. As the floss is withdrawn from the dispenser, the arms rock from side to side moving the floss across the teeth of the animated figure in simulation of the flossing operation.

The mechanism for rocking the arms 15 from side to side upon the removal of dental floss 16 from a roll or spool 17 thereof comprises a rocker disc 18 and a plate or cam wheel 19. These parts together with the forward and rear members 11A and 11B, respectively, of the housing 11, an animated face disc 21, a transparent cover 22 and a single screw 23 comprise the total set of individual parts making up the dispenser 10.

The housing 11 as shown in the frontal view of FIG. 1 has an outline approximating the head and shoulders of the animated character. The underside 24 is flat to permit the housing 11 to stand upright on a flat surface. The forward and rear members 11A and 11B constitute hollow shells that fit together all about their peripheries in a locking manner to form between them the cavity 12. Horizontal shelves 25 extending inwardly towards each other at an elevation approximately one third the height of the dispenser 10 form in the lower portion of the cavity 12 a storage compartment 12B for the roll of floss 17 and in the upper portion, a chamber 12A for the mounting and containment of the rocker disc 18 and cam wheel 19. The shelves 25 stop short of meeting each other, leaving a slot 26 for the passage of floss from compartment 12B to chamber 12A.

The chamber 12A is approximately circular, and at the center of the circle, a cylindrical post 27 extends rearward from the forward wall of the forward member 11A. Aligned with post 27 and extending forward from the rear wall of rear member 11B is a second cylindrical post 28. The two posts 27 and 28 have equal diameters, and they meet at the plane defining the interface between members 11A and 11B. Together, the posts 27 and 28 serve as a pivotal mounting for cam wheel 19. Post 27 has an axial threaded hole 29 for screw 23 while post 28 has an axial clearance hole 31 for screw 23 that is aligned with hole 29. When members 11A and 11B are placed together with their open edges abutting, the screw 23 may be inserted through hole 31 from the rear of dispenser 10. Screw 23 is then threaded into hole 29 and tightened to hold the forward and rear members 11A and 11B together.

Circular depressions 32 are formed into both side walls of forward member 11A. The two depressions 32 which are directly opposite each other, hold the ends of the spool or carrier 33 upon which the spool of floss 17 is wound. The depressions 32 are open at the side facing the edge of member 11A to permit the installation of the spool 33 into the slots 32 during the assembly of the dispenser 10.

A flat circular depression 35A covers most of the upper portion of the front surface of member 11A. The depression is bounded by a small ridge 36 which completely surrounds the depression. Outlining the face of the animated character, a like depression 35B is formed into the rear surface of rear member 11B. An upward projection 37 above the depression 35A simulates a hat or crown; the lower and broader portion of the housing lying below the depression 35 represents the shoulders 38 of the animated character.

Directly below post 27 in the front face of member 11A within the bounds of the depression 35 is a circular hole 39. An annular depression in the forward surface of member 11A extending about the circumference of hole 39 forms a shoulder or cavity 40 which serves as a rotational retainer for rocker disc 18.

The forward edge of rear member 11B is notched at both sides of the circular upper portion, the notches 41 serving as exit ports or apertures for the dental floss as it is drawn from the dispenser 10. The aperture or notch 41 to the right side of the face is more convenient for use by right-handed users, while the notch to the left side is more convenient for someone who is left handed.

Cam wheel 19 has a central platform 42 in the form of a flat circular disc. Extending rearward from the center of platform 42 is a cylindrical shell 43, the central opening 44 of which extends forward through platform 42. The cylindrical opening 44 fits over posts 27 and 28 in the assembled dispenser, the posts 27 and 28 serving as a rotational mounting for cam wheel 19. A contoured projection 45 surrounds the opening 44 on the forward surface of platform 42, the projection 45 serving as a cam for the actuation of rocker disc 18. As shown in FIG. 3, the general outline of projection 45 approximates a square with the four corners 46 rounded and with the four sides depressed slightly forming shallow concave surfaces 47 rather than straight sides.

Rocker disc 18 also has a central platform 48 in the form of a flat circular disc 49 that is considerably smaller than platform 42. Extending rearward from the rear surface of platform 48 are two pegs 51 and 52 which are engaged in the assembled dispenser 10 by the cam wheel 19. The pegs are positioned at opposite ends of a horizontal line that crosses circular platform 48 just above its center. Extending forward from the bottom edge of the forward surface of platform 48 is a short projection 53, not more than one sixteenth of an inch in height which serves as a mounting post for the arms 15 and hands 13 of the animated figure. A planar representation of the arms and hands utilizes a curved band 54 to represent the arms, the center of the band 54 being supported by projection 53. The hands 13 extending from the ends of band 54 appear to be holding a length of dental floss 55. The planar representation of the arms and hands lies in a plane that is parallel with circular platform 48.

Animated face disc 21 is generally circular with a diameter just slightly smaller than that of depression 35A. A representation of the face of the animated character with the teeth bared, is printed on the front surface of disc 21. A broad notch 56 is cut into the lower edge of disc 21, the notch 56 forming an opening for the passage therethrough of projection 53 of rocker disc 18 in the assembled dispenser 10.

Cover 22 is of transparent plastic and shaped in the form of a circular watch crystal. Three retainer tabs 57 uniformly spaced at 120 degrees about the circumference of cover 22 mate with slots 58 at the edge of depression 35A.

To assemble the dispenser 10, the spool of floss 17 is first installed in the lower cavity 12B with the ends of spool 33 positioned in the depressions 32. Cam wheel 19 is then installed over post 27 with projection 45 facing forward. The free end of the floss 16 is then routed over the top of shell 43 of cam wheel 19 and out through one of the notches 41. Rear member 12B is then put in place and secured to member 12A by installing screw 23. Face disc 21 is then positioned between platform 42 and band 54 of rocker disc 18 with notch 56 receiving projection 53 and with the printed surface of disc 21 facing the arms 15 and hands 13. The assembled discs 18 and 21 are next installed in depression 35A with platform 48 fitting into cavity 40. Finally, cover 22 is pressed into place inside depression 35B, its three tabs snapping into the slots 58 which retain the cover 22. Cover 22 now retains in position the face disc 21 and the rocker disc 18.

It will now be observed that as the floss 16 is drawn from the dispenser 10 through the notch 41, its passage over the top surface of shell 43 causes wheel 19 to rotate in the direction of the arrow 59, shown in FIGS. 6–12. As shown in the same figures, the peripheral surfaces of projection 45 maintain contact with the edges of the pegs 51 and 52 as cam wheel 19 is rotated. Binding or jamming between the pegs 51 and 52 and the projection 45 is prevented by virtue of the geometry of the contours and also by virtue of the relatively loose or non-rigid mounting of disc 18 and wheel 19 which permits the two parts to yield as necessary in the event that any interference begins to develop.

FIGS. 6–12 illustrate successive rotational positions of the cam wheel 19 and the resulting positions of rocker disc 18 as disc 18 is rocked from side to side by the rotation of wheel 19. As an aid in the description of this action, the four corners 46 of projection 45 are numbered 1–4, and a line 61 is drawn through the centers of the pegs 51 and 52 to indicate the rotational position of rocker disc 18.

Figure 6:
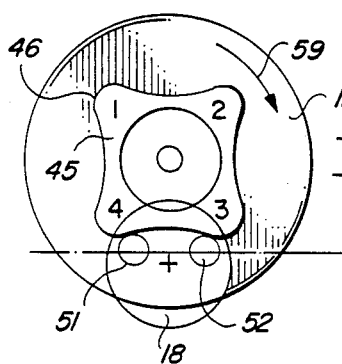
Figure 10:
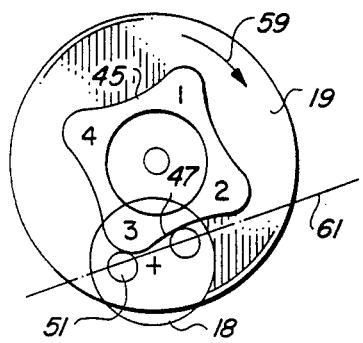

In the starting position shown in FIG. 6, corners 3 and 4 are aligned horizontally and pegs 51 and 52 are both in contact with the horizontally oriented concave surface 47 so that line 61 is horizontal. In this position of rocker disc 18, the hands 13 and the length of dental floss 55 are also horizontally aligned.

Figure 7:
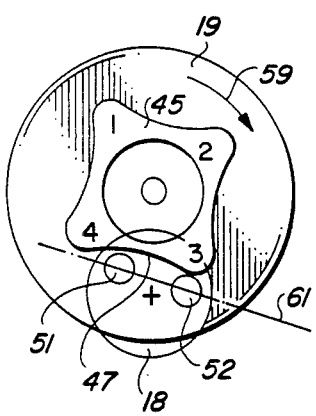
Figure 11:
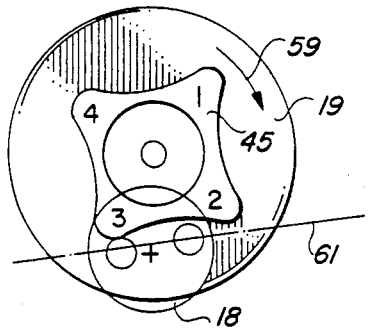

In FIG. 7, wheel 19 has rotated approximately twenty degrees clockwise from the position of FIG. 6. Corner 3 has moved peg 52 downward and peg 51 has moved upward into the concave surface 47 between corners 3 and 4. Line 61 has consequently rotated clockwise with an attending tilting to the right of the arms 15 and hands 13 as viewed from the rear.

Figure 9:
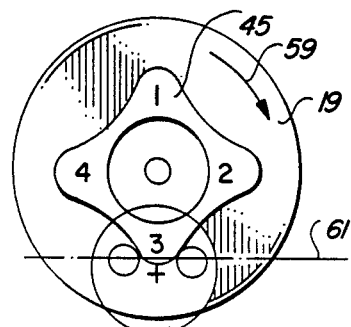
FIGS. 6-12 are illustrative of the sequential action of the cam wheel of FIG. 3 in cooperation with a rocker arm which together produce the animated movement in simulation of the flossing action.
Figure 8:
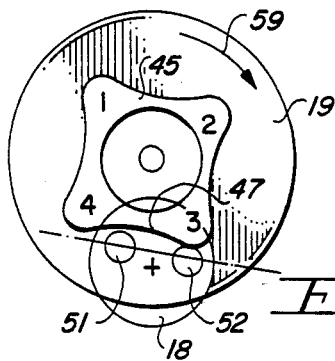

The same action continues in FIGS. 8 and 9. As corner 3 passes over peg 51 and falls between pegs 51 and 52, as shown in FIG. 9, disc 18 rotates counter-clockwise with line 61 returning to the initial horizontal orientation.

Further rotation of wheel 19 in the direction of arrow 59 moves corner 3 against peg 51 driving peg 51 downward and allowing peg 52 to move upward into the concave surface between corners 2 and 3. Line 61 and rocker disc 18 are thus now tilted to the left along with the arms 15.

Figure 12:
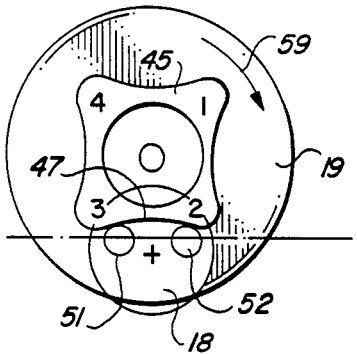

Continued rotation of wheel 19 in the direction 59, as shown in positions 11 and 12, returns disc 18 and line 61 to the horizontal alignment of FIG. 12 in which pegs 51 and 52 both abut the concave surface 47 between corners 2 and 3.

Ninety degrees of rotation of wheel 19 has been illustrated by the successive views of FIGS. 6–12. During the course of this ninety degrees of rotation, the arms 15 have been tilted first to the right from the initial upright position, then back to an upright position, then to the left, and again back to an upright position. Each successive ninety degrees of rotation causes the arms to tilt once to the right and once to the left. For each 360 degrees of wheel 19, four such full tilting cycles of the arms 15 are thus produced so that the removal of a relatively short length of floss 16 produces many cycles of such tilting action and consequently a very animated action which simulates the flossing of the teeth of the animated character.

Once the desired length of floss 16 has been withdrawn from the dispenser 10, it is drawn into a wedge shaped cutter 62. One such cutter 62 is provided at each side of housing 11 near its mounting surface 24.

The dispenser 10, as shown, comprises a small number of relatively simple parts that may be very inexpensively molded in a plastic material. Its assembly is very easily and quickly accomplished and is secured by a single screw. As a consequence, the cost is low so that a very marketable product results.

An effective and inexpensive dental floss dispenser is thus provided in an animated form that encourages its use in accordance with the stated objects of the invention, and although but a single embodiment of the invention has been illustrated and described, it will be apparent to those skilled in the art that various changes and modifications may be made therein without departing from the spirit of the invention or from the scope of the appended claims.

What is claimed is:

1. An animated dental floss dispenser comprising:
   a hollow housing displaying an animated character on one outer surface thereof and having a simulated open mouth showing its teeth,
   a slot formed in said surface immediately below the teeth of said character,
   a pair of spaced hands having a simulated piece of dental floss extending therebetween mounted in front of said mouth and having a pair of spaced pins mounted thereon to extend through said slot and into said housing,
   a cam wheel mounted behind said animated character and in said housing,
   cam means mounted on said cam wheel for engaging said pins and moving said pins to cause said hands to move back and forth through an arcuate path in front of said teeth simulating a tooth flossing operation,
   said cam means comprising a surface for engaging a piece of floss passing thereover for rotation of said cam means upon predetermined movement of a piece of said floss out of said housing, and
   a spool of floss mounted in said housing adjacent said cam means,
   said housing having a first aperture extending therethrough,
   whereby when a piece of the floss from said spool is fed over said surface and through said first aperture and is pulled outwardly of said housing, its movement causes rotation of said cam means and movement of said hands simulating the flossing of the teeth of the animated character.

2. The animated dental floss dispenser set forth in claim 1 wherein:
   said spool of floss is rotatably mounted in said housing.

3. The animated dental floss dispenser set forth in claim 1 wherein:
   rotative movement of said cam means causes a pendulum movement of said spaced hands.

4. The animated dental floss dispenser set forth in claim 1 in further combination with:
   said housing having a second aperture extending therethrough and spaced from said first aperture,
   said floss being fed through a particular one of said apertures depending on whether the dispenser is intended to be used by a right or left handed user.

5. The animated dental floss dispenser set forth in claim 1 wherein:
   said cam means comprises a square configuration.

6. The animated dental floss dispenser set forth in claim 1 wherein:

said cam comprises a four cornered configuration.

7. The animated dental floss dispenser set forth in claim 1 wherein:
said spaced hands are fixedly attached to move in an arcuate path in front of said teeth.

8. The animated dental floss dispenser set forth in claim 1 in further combination with:
a disc having an animated face illustrated thereon,
said disc being positioned over said one outer surface, and
a transparent cover mounted over said disc and attached to said housing.

* * * * *